US 8,488,862 B2

(12) United States Patent
Bose et al.

(10) Patent No.: US 8,488,862 B2
(45) Date of Patent: Jul. 16, 2013

(54) CHARACTERIZATION OF SOURCE TRAJECTORY FOR RADIOTHERAPY

(75) Inventors: Supratik Bose, Walnut Creek, CA (US); Himanshu P. Shukla, Lafayette, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 614 days.

(21) Appl. No.: 12/797,093

(22) Filed: Jun. 9, 2010

(65) Prior Publication Data
US 2011/0305380 A1 Dec. 15, 2011

(51) Int. Cl.
*G06K 9/00* (2006.01)
*H01J 35/00* (2006.01)
*H05G 1/28* (2006.01)

(52) U.S. Cl.
USPC ............ 382/132; 378/132; 378/163; 378/164

(58) Field of Classification Search
USPC .................................. 382/132; 378/163, 164
See application file for complete search history.

(56) References Cited

U.S. PATENT DOCUMENTS

| | | | |
|---|---|---|---|
| 7,349,523 B2* | 3/2008 | Jenkins et al. ................... | 378/65 |
| 2004/0264648 A1* | 12/2004 | Claus et al. ..................... | 378/163 |
| 2005/0117708 A1* | 6/2005 | Cho et al. ....................... | 378/164 |
| 2006/0122502 A1 | 6/2006 | Scherch et al. | |
| 2006/0215813 A1 | 9/2006 | Scherch et al. | |
| 2011/0249882 A1* | 10/2011 | Bornfleth ....................... | 382/132 |

OTHER PUBLICATIONS

Gonzalez, et al., *A Procedure to Determine the Radiation Isocenter Size in a Linear Accelerator*, Medical Physics, vol. 31, No. 6, Jun. 2004, pp. 1489-1493.
Skworcow, et al. *A New Approach to Quantify the Mechanical and Radiation Isocenters of Radiotherapy Treatment Machine Gantries*, Physics in Medicine and Biology, vol. 52 (2007), IOP Publishing, doi: 10.1088/0031-9155/52/23/022, pp. 7109-7124.
*Diameter of the Radiation Isocenter*, Retrieved May 25, 2010, Retrieved from Internet: http://www.wienkav.at/kav/kfj/91033454/physik/aS500_sphere.html, 10 pages.
Lutz, et al., *A system for stereotactic radiosurgery with a linear accelerator*, International Journal of Radiation: Oncology Biology Physics, Pergamon Press, USA, vol. 14, No. 2, Feb. 1, 1988, pp. 373-381, XP026844532, ISSN: 0360-3016.
EP Search Report dated Sep. 16, 2011 from counterpart EP application No. 11168965.9-2305, 6 pages total.

* cited by examiner

*Primary Examiner* — Neal Sereboff

(57) ABSTRACT

Some embodiments include obtaining a projection image of a plurality of fiducials associated with a coordinate system irradiated by a radiotherapy radiation source at a plurality of discrete locations on a trajectory path model, determination of a projection matrix from projection images of the fiducials irradiated by the radiotherapy radiation source at each of the discrete locations, determination of the actual coordinate of the radiotherapy radiation source in the coordinate system associated with the fiducials at the plurality of discrete locations based on the determined projection matrices, and correlating the trajectory path model of the radiotherapy radiation source to the determined actual position of the radiotherapy radiation source at the discrete locations.

17 Claims, 6 Drawing Sheets

CHARACTERIZATION OF SOURCE TRAJECTORY FOR RADIOTHERAPY

BACKGROUND

1. Field

The embodiments described herein relate generally to radiotherapy systems. More particularly, the described embodiments relate to providing an accurate independent measurement of a source trajectory for radiotherapy systems.

2. Description

Radiotherapy or radiation therapy is used to treat cancer and other diseases with ionizing radiation. A linear accelerator may be used to produce electrons or photons having particular energies. In one common application, a linear accelerator generates a radiation beam and directs the beam toward a target area of a patient. The beam is intended to injure or destroy cells within a target area by causing ionizations within the cells or other radiation-induced cell damage.

Radiation treatment plans are intended to maximize radiation delivered to a target while minimizing radiation delivered to healthy tissue. To design an effective radiation treatment plan, a designer must assume that the location and movement of the radiation source can be precisely known and controlled and that relevant portions of a patient will be in particular positions relative to the radiation source during delivery of the treatment radiation. The goals of maximizing target radiation and minimizing healthy tissue radiation may not be achieved if the location and movement of the radiation source are not positioned in accordance with the treatment plan during delivery of the radiation. More specifically, errors in positioning the radiation source can cause the delivery of low radiation doses to tumors and high radiation doses to sensitive healthy tissue. The potential for misdelivery increases with increased positioning and tracking (i.e., trajectory path) errors.

In a common embodiment of a radiotherapy system, a single radiation source is moved in a planar circular orbit about a target treatment area. The radiation is delivered in a cone from a fixed distance along a central axis at different positions along the circular orbit. Radiation delivered from the different positions ideally intersect or converge at a single point or cloud of points in space. That single point or cloud in space is referred to as the isocenter.

Conventional radiotherapy systems may be used to verify the position of the radiation source prior to delivery of treatment radiation to a patient. The verification is intended to confirm that the radiotherapy radiation is precisely delivered to relevant portions of a patient that will be positioned in accordance with a treatment plan. Some prior radiotherapy systems used film to detect the isocenter of the radiation. For example, the Winston-Lutz test may be used to verify the mechanical accuracy of the isocenter in radiotherapy.

However, the Winston-Lutz test and other procedures for determining and verifying the isocenter in radiotherapy have a number of limitations. Some procedures are limited to using radiograph film or other specific types of radiation detectors. As such, the accuracy of the isocenter determination is limited by the imaging resolution of the other specific types of radiation detectors and other physical limitations thereof (e.g., positioning, sensitivity, etc.) Some methods are limited to particular radiotherapy radiation source trajectories, either circular or non-circular. As such, the determination of the radioptherapy isocenter and thus the determination of the location of the radiation source is dependent on, for example, the radiotherapy radiation source trajectories of interest.

Systems are therefore desired for efficient determination of radiotherapy radiation source trajectory measurements.

SUMMARY

In order to address the foregoing, some embodiments provide a system, method, apparatus, and means to obtain a projection image of a phantom having a plurality of fiducials at known reference positions in a coordinate system associated with the phantom irradiated by a radiotherapy radiation source at a plurality of discrete locations of a trajectory path model, determine a projection matrix from the projection image corresponding to each discrete location of the trajectory model, determine the actual coordinate of the radiotherapy radiation source in the coordinate system associated with the phantom at each of the discrete locations based on the determined projection matrices, and correlate the trajectory path model of the radiotherapy radiation source to the determined actual position of the radiotherapy radiation source at the plurality of discrete locations.

Some aspects include obtaining a trajectory path model for the radiotherapy radiation source where the trajectory path model is defined by at least one parameter, determining each of the plurality of discrete location, and providing an output of at least one variance between the trajectory path model of the radiotherapy radiation source and the determined actual position of the radiotherapy radiation source at each of the discrete locations.

Some embodiments include the trajectory path model being one of a circular trajectory and a non-circular trajectory. In some aspects, the output may include providing at least one of a numerical and a graphical presentation of a variance in trajectory and the at least one parameter of the trajectory path model for the determined actual position of the radiotherapy radiation source at the plurality of discrete locations. Additionally, the system, method, apparatus, and means herein may be used independent of and in combination with an imaging calibration procedure.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
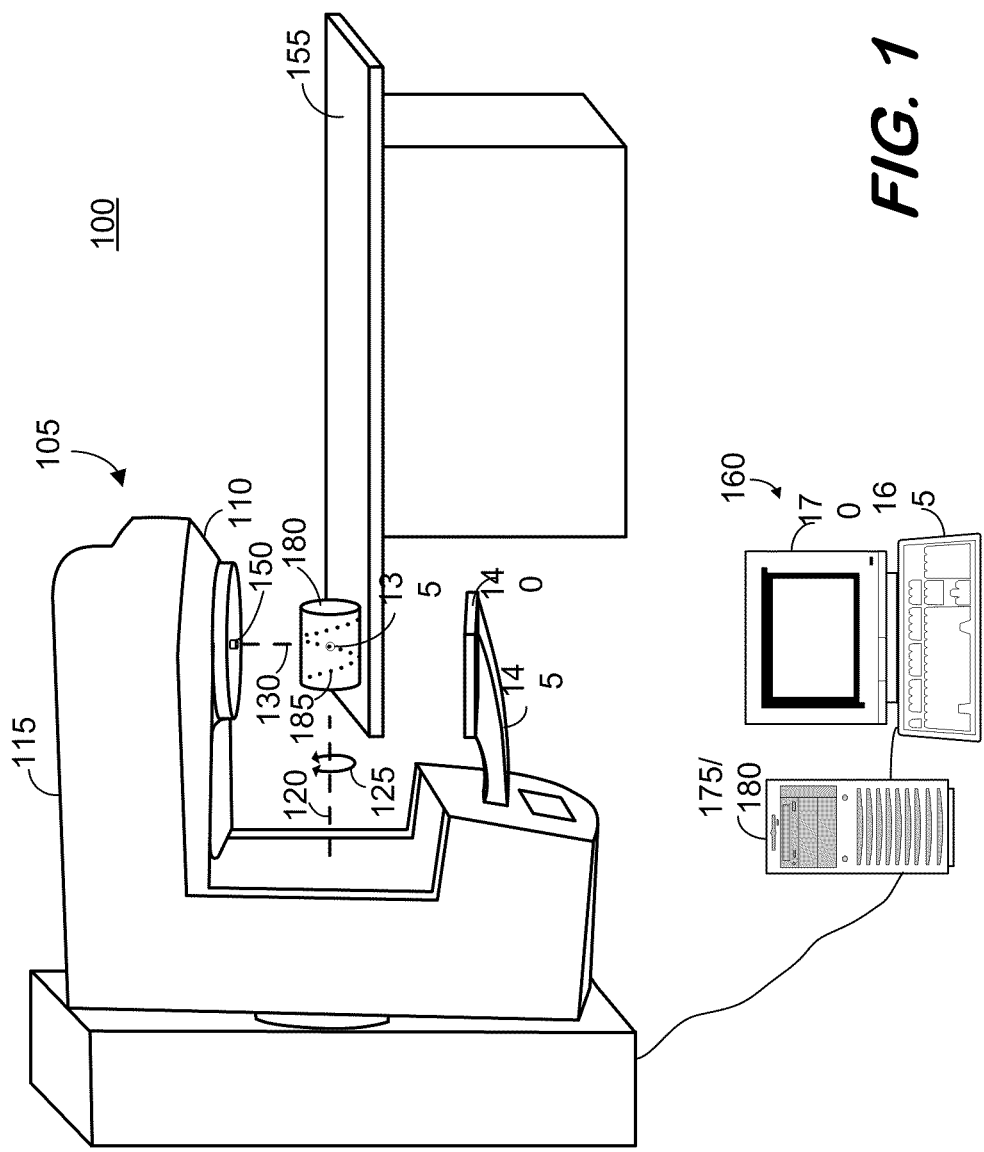
FIG. 1 is a perspective view of a radiotherapy system according to some embodiments.

FIG. 1 illustrates radiotherapy treatment room 100 pursuant to some embodiments. Radiotherapy treatment room 100 includes linear accelerator (linac) 105, table 155 and operator console 160. The various components of radiotherapy treatment room 100 may be used to deliver a beam of radiation to a target volume such as phantom 180. The target volume may comprise a patient positioned to receive the beam according to a radiation treatment plan. The elements of treatment room 100 may be employed in other applications according to some embodiments.

Linac 105 generates and emits a radiation beam (e.g., an x-ray beam) from treatment head 110. More particularly, the radiation originates at radiation source 150. The radiation beam may comprise electron, photon or any other type of radiation. According to some embodiments, the beam exhibits energies in the megavoltage range (i.e. >1 MeV) and may therefore be referred to as megavoltage beam.

Treatment head 110 is coupled to a projection of gantry 115. Gantry 115 is controllable to be rotatable around gantry axis 120. As indicated by arrow 125, gantry 115 may rotate clockwise or counter-clockwise according to some embodiments. Rotation of gantry 115 serves to rotate treatment head 110 around axis 120.

During radiation emissions (e.g., treatment, calibration, and other procedures) treatment head 110 emits a divergent beam of megavoltage x-rays along beam axis 130. The beam is emitted towards isocenter 135 of linac 105. Isocenter 135 may be located at the intersection of beam axis 130 and gantry axis 120. Due to divergence of the beam and the shaping of the beam by beam-shaping devices in treatment head 110, the beam may deliver radiation to a volume of phantom 180 rather than only through isocenter 135.

Table 155 may support a patient during radiation treatment and support phantom 180 during aspects discussed herein. Table 155 may be adjustable to assist in positioning phantom 180 or a particular target volume of a patient at isocenter 135. Table 155 may also be used to support devices used for such positioning, for calibration and/or for verification.

Imaging device 140 may comprise any system to acquire an image based on received radiation. Imaging device 140 may be attached to gantry 115 in any manner, including an extendible and retractable housing 118. Rotation of gantry 115 may cause treatment head 110 and imaging device 140 to rotate around isocenter 135 such that isocenter 135 remains located between treatment head 110 and imaging device 140 throughout stationary and rotational movements of gantry 115.

Imaging device 140 may acquire projection images before, during and/or after radiation treatment. In some embodiments, imaging device 140 may include an analog or a digital radiation detector. Imaging device 140 may be used to acquire images based on radiation emitted from treatment head 110. These images may reflect the attenuative properties of objects located between treatment head 110 and imaging device 140. As will be described below, such projection images may be used to determine imaging geometry parameters associated with the imaging system consisting of treatment head 110 and imaging device 140. The two-dimensional projection images and/or three-dimensional images reconstructed based on the projection images may be used to verify and record a target volume (e.g., a phantom 180) position and a position of a marker (e.g., a fiducial 185) in the target volume, from which the location of the radiation source 150 may be determined.

Radiation source 150 may include any sources to emit kilovoltage radiation or other imaging radiation that are or become known. In some embodiments, radiation source 150 may employ a cathode based on carbon nanotube or thermionic emission technology. In some embodiments, each radiation source 150 is disposed in a fixed relationship with respect to treatment head 110.

Imaging device 140 may be used to acquire a projection image based on radiation emitted from radiation source 150. These projection images may reflect the attenuative properties of objects (e.g., phantom 180) located between radiation source 150 and imaging device 140, including conveying the position of fiducials in the objects. These projection images may be used to determine imaging geometry parameters associated with the imaging system including radiation source 150 and imaging device 140.

It is noted that the source-detector trajectory of the radiotherapy system including the imaging system may be controlled, in some embodiments, to move in a circular or non-circular trajectory and/or have a fixed or variable radiation source-detector distance.

Figure 2:
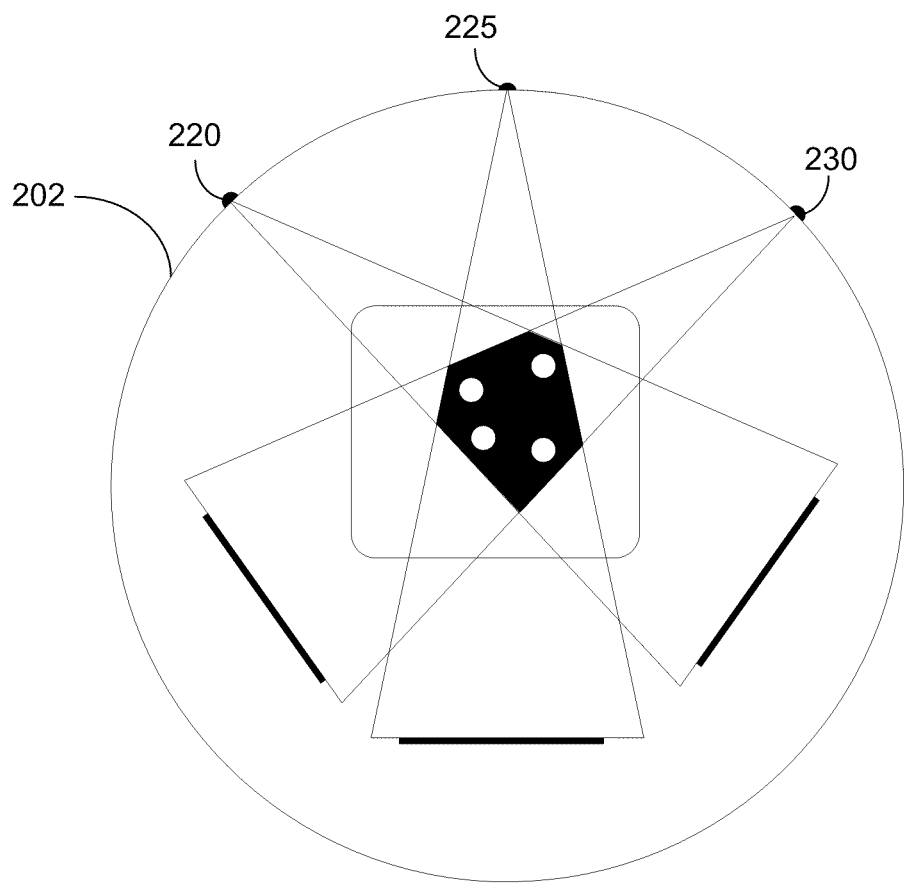
FIG. 2 is an illustrative example of a fixed source-detector distance, isocentric trajectory according to some embodiments.

FIG. 2 is an illustrative example of a fixed radiation source-detector distance, isocentric trajectory 200, with radiation cones 205, 210, 215 through a phantom 235 including a number of fiducials 245. As shown, trajectory 200 has a circular orbit 202 and the radiation source emits radiation at discrete locations 220, 225, and 230 on the trajectory 200. Moreover, the isocenter is represented at 240. The isocenter represents the parameter that defines the coordinate of the center of the fitted circular trajectory.

Figure 3:
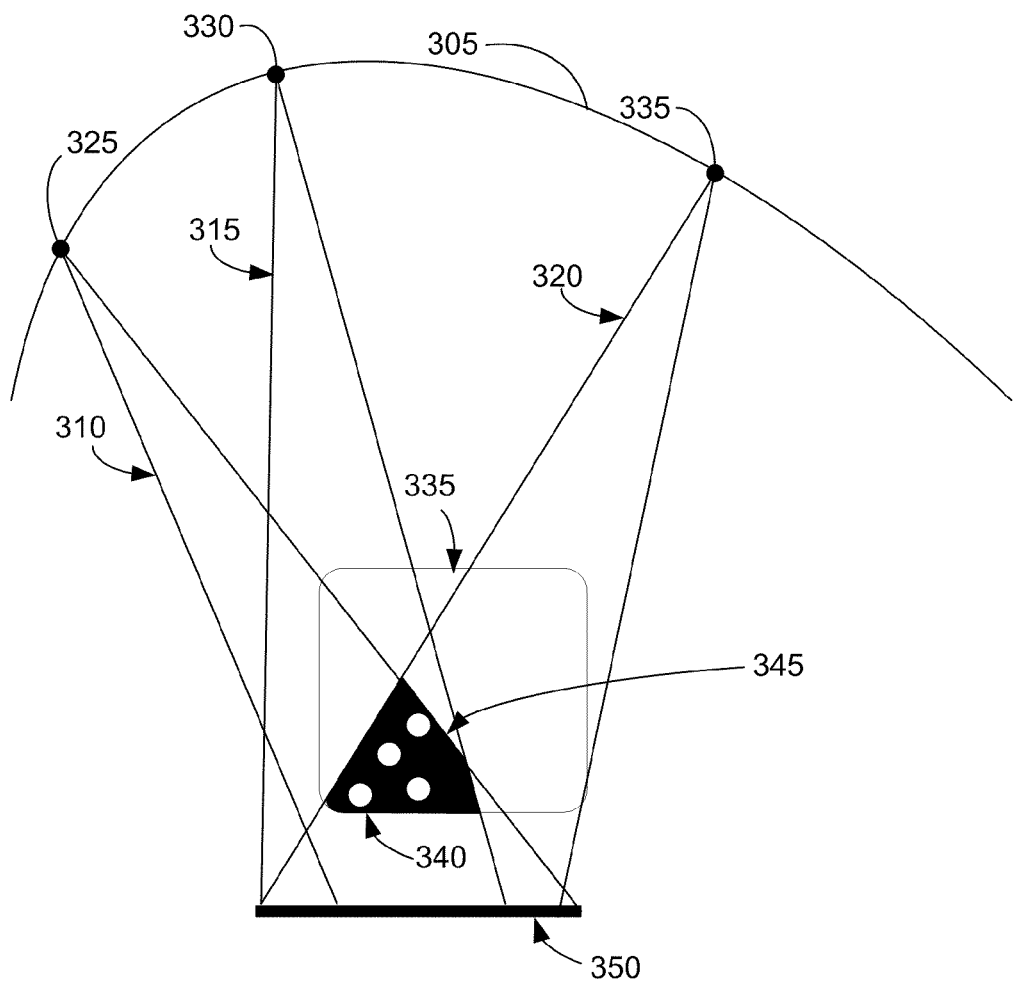
FIG. 3 is an illustrative example of a variable source-detector distance, trajectory according to some embodiments.

FIG. 3 is an illustrative example of a variable radiation source-detector distance, trajectory 300 used with a fixed detector 350. As shown, radiation cones 310, 315, and 320 are emitted through a phantom 335 including a number of fiducials 340 from a number of discrete locations 325, 330, and 335. As shown, trajectory 300 has a variable distance trajectory path 305 with respect to the fixed position detector 350. The isocenter is represented at 345 and represents the coordinate of the focus point of the fitted parabolic trajectory.

Operator console 160 includes input device 165 for receiving instructions from an operator such as an instruction to calibrate linear accelerator 105 and an instruction to move radiation source 150 in a particular trajectory and to deliver radiation from a number of discrete locations along the trajectory path, according to a trajectory path and model. Console 160 also includes output device 170 that may include a monitor for presenting calculated projection images, acquired projection images, three-dimensional images, operational parameters of linear accelerator 105 and/or interfaces for controlling elements thereof. Input device 165 and output device 170 are coupled to processor 175 and storage 180.

Processor 175 executes program code according to some embodiments. The program code may be executable to control linear accelerator 105 to operate as described herein. The program code may be stored in storage 180, which may comprise one or more storage media of identical or different types, including but not limited to a fixed disk, a floppy disk, a CD-ROM, a DVD-ROM, a Zip™ disk, a magnetic tape, a solid state storage device, a flash drive, and a signal. Storage 180 may store, for example, virtual models of phantoms, initial imaging geometry parameters, radiation treatment plans, projection images, software applications to calibrate linear accelerator 105 and/or to provide radiation treatment, and other data used to perform radiation treatment.

Operator console 160 may be located apart from linear accelerator 105, such as in a different room, in order to protect its operator from radiation. For example, linear accelerator 105 may be located in a heavily shielded room, such as a concrete vault, which shields the operator from radiation generated by accelerator 105.

Each of the devices shown in FIG. 1 may include less or more elements than those shown and are not limited to the devices shown in FIG. 1.

Figure 4:
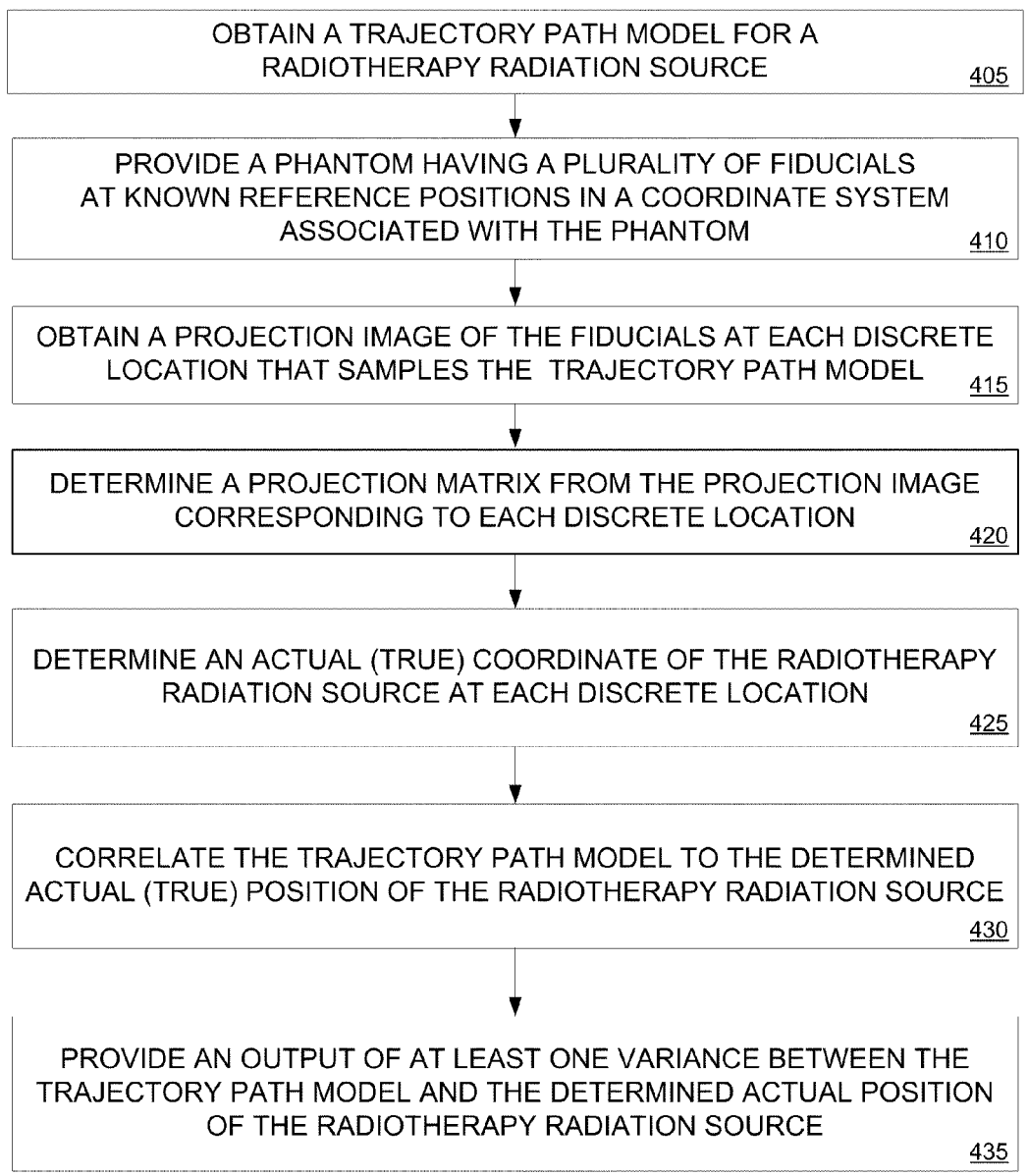
FIG. 4 is a flow diagram of process steps pursuant to some embodiments.

FIG. 4 is a flow diagram of a process according to some embodiments. Process 400 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, a solid state storage device, or a signal. Examples of these processes will be described below with respect to the elements of radiotherapy treatment room 100, but embodiments are not limited thereto.

Process 400 may be performed at any time, including during initial installation of linear accelerator 105 in radiotherapy treatment room 100. Process 400 may be performed periodically according to a quality assurance, maintenance, or certification schedule, and/or prior to each radiation treatment fraction.

In some embodiments, and prior to operation 405, an operator may manipulate input device 165 of operator console 160 to initiate operation of linear accelerator 105. In response, processor 175 may execute program code of a system control application stored in storage 180. The operator may then operate input device 165 to initiate process 400.

At 405, a trajectory path model for radiotherapy source 150 may be obtained. The trajectory path model is defined by at least one parameter. In the example of a circular orbit trajectory with an isocenter at a fixed distance from the source (e.g., FIG. 2), the at least one parameter may include a radius or diameter of the circular orbit trajectory. In the instance of other trajectory path models, the at least one parameter may include other parameters including, but not limited to, start and stop coordinates, start and stop angles, and equations describing the trajectory of the trajectory path model. The trajectory path model may be selected based on a number of factors and considerations, including for example, a treatment plan and a capability of linear accelerator 105. For example, the trajectory path model may be one of a circular orbit or a non-circular orbit.

In some embodiments, process 400 is not constrained a particular type or types of trajectories. Accordingly, the trajectory path model obtained at 405 may include any trajectory path model. As a practical matter, the trajectory path model includes a trajectory path which linear accelerator 105 may be controlled to execute.

At operation 410, a phantom is provided and positioned on support table 155. The phantom includes a plurality of fiducials or markers in and/or thereon. The fiducials are positioned at known positions in a coordinate system associated with the phantom. In some aspects, the coordinate system may further be related to radiotherapy treatment room 100.

At operation 415, a projection image of the fiducials irradiated by the radiotherapy radiation source is obtained at each of a plurality of discrete sampling locations along the trajectory path model. The radiotherapy radiation source is sequentially moved to a number of discrete sampling locations along the trajectory path model and the fiducials are irradiated at each location, thereby creating a 2D projection image that is detected at imaging device 140. The projection image is determined based on the imaging geometry parameters associated with the linear accelerator 105 and the trajectory path model.

According to the present example of process 400, a projection image of fiducials 185 is determined at 415 based on imaging geometry parameters associated with the imaging system including of treatment head 110, imaging device 140, and the trajectory path model. Storage 180 may store initial (or model) imaging geometry parameters associated with the imaging system, the trajectory path model, and the sampling locations on the trajectory path model for irradiating the fiducials.

At operation 420, a projection matrix may be created from the projection image corresponding to each discrete sampling location of the trajectory path model. The projection matrices determine the 2D coordinate of the projection in the projection of any 3D point in the coordinate system associated with the phantom generated by the radiotherapy source at that discrete location in the trajectory path model.

Figure 5:
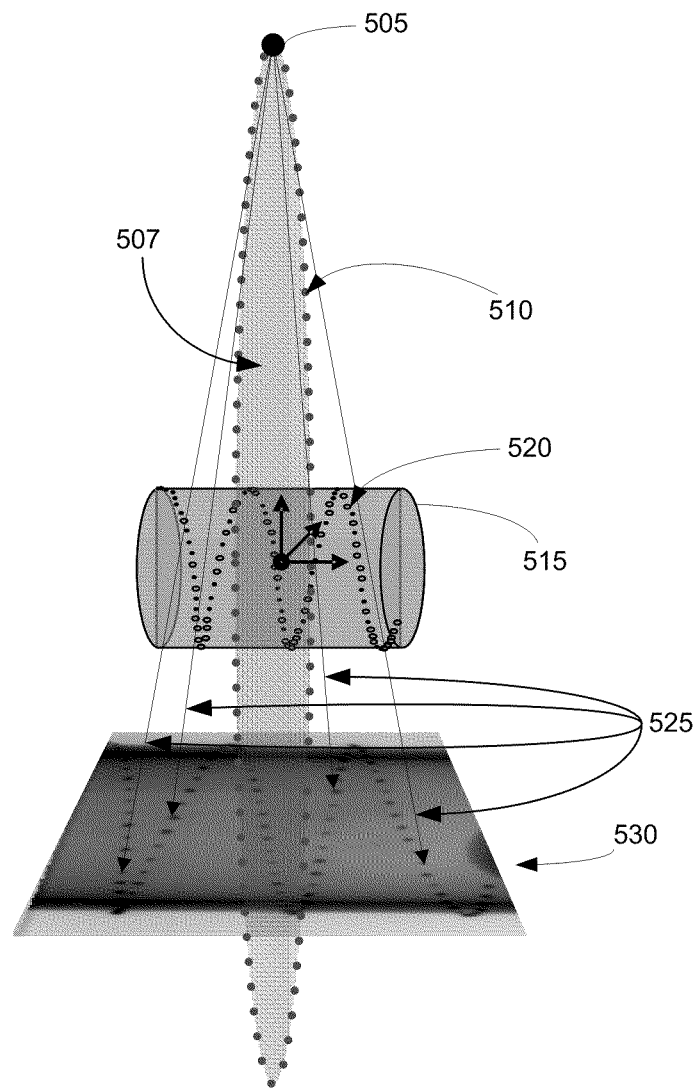
FIG. 5 is an illustrative depiction of a radiotherapy radiation source and a projection image and calculated projection matrix according to some embodiments.

FIG. 5 is an illustrative depiction of a radiotherapy radiation source and a projection image and calculated projection matrix according to some embodiments, generally represented at 500. As illustrated, a radiation source 505 emits a radiation beam 507 at one of the discrete sampling locations located on trajectory path model 510. It is noted that the discrete sampling locations represented by the dots on trajectory path model 510 may include more or fewer locations than those depicted in FIG. 2 and are provided for illustrative purposes. Furthermore, phantom 515 includes a plurality of fiducials therein. Fiducial 520 is but one representative fiducial in the phantom. Only one fiducial (i.e., 520) is referenced in FIG. 2, so as not to obscure other features of the drawing.

Further shown is a coordinate system associated with the fiducials. The coordinate system in this example is shown located at about a center location of phantom 515. As discussed earlier, the coordinate system is associated with the phantom and in accordance with aspects herein, the fiducials are located at known reference positions with respect to this coordinate system.

Projections 525 are based on the radiation irradiated on fiducials 520 by the radiotherapy radiation source at sampling location 505. The projections are detected and projection image 530 is acquired for the radiotherapy radiation source at the shown sampling location. Projections 525 on the 2D projection image 530 may be used to determine a projection matrix and the source location in the 3D coordinate system associated with phantom 515. The source location is determined based on the projection matrix determined from each projection image associated with each sampling location on the trajectory path model. As illustrated, the multiple projections 525 meet at the radiation source.

Returning to process 400 and operation 425 in particular, an actual, true, coordinate of the radiotherapy radiation source in the coordinate system associated with the phantom is determined at each sampling location, based on the projection matrix determined at operation 420. The actual true coordinate is thus a 3D representation of the location of the radiotherapy radiation source.

At operation 430, the trajectory path model of the radiotherapy radiation source is correlated to the determined actual coordinate position of the radiotherapy radiation source at the plurality of discrete sampling locations included in process 400. The correlating may include a fitting procedure to fit the trajectory path model to the true determined actual coordinate positions of the radiotherapy radiation source at the plurality of discrete sampling locations. In some embodiments, the fitting procedure may include a least squares fitting procedure. Other mathematical procedures in addition to or in lieu of the least squares fitting procedure may be used for fitting the trajectory path model of the radiotherapy radiation source to the determined actual coordinate position of the radiotherapy radiation source at the plurality of discrete sampling locations.

At operation 435, an output of some indicator of a variance between the trajectory path model of the radiotherapy radiation source and the determined actual coordinate position of the radiotherapy radiation source at the plurality of discrete sampling locations is provided. The output may be provided as a numerical and/or graphical presentation at output device 170. In some aspects, the output will relate to the at least one parameter that defines the trajectory path model. The deviation of individual source positions from the fitted trajectory path model can be calculated, analyzed and presented in the output. The output may include data including, but not limited to, the fitted model and the trajectory path model, as well other information.

Figure 6:
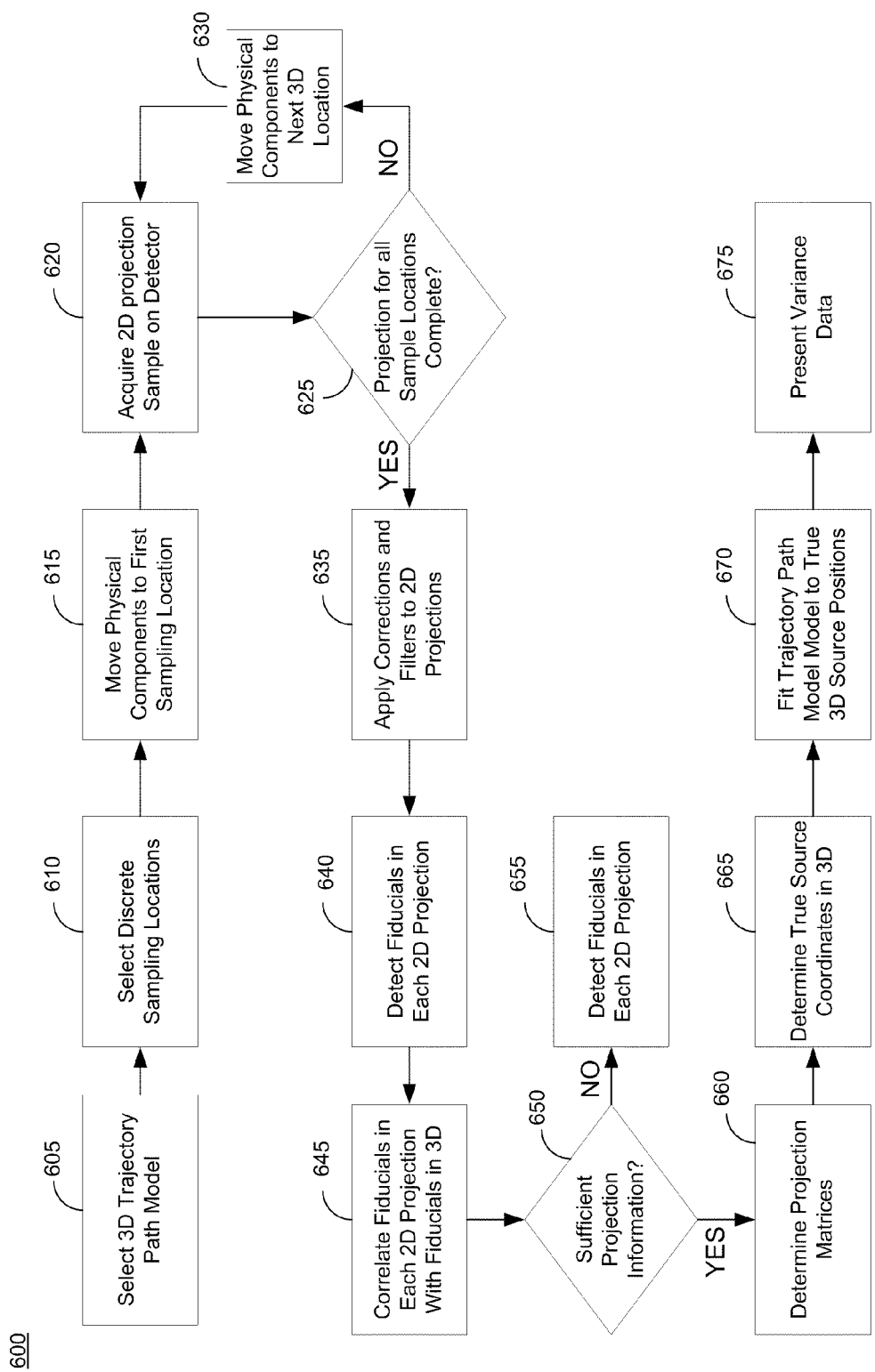
FIG. 6 is a flow diagram of process steps pursuant to some embodiments.

FIG. 6 is a flow diagram of a process according to some embodiments. Process 600 is similar in some aspects to the flow of FIG. 4 but includes some aspects not directly depicted therein.

At 605, a trajectory path model for radiotherapy source 150 is obtained. The trajectory path model is defined by at least one parameter and may be obtained from storage device 175 and/or provided by another system or source (not shown).

At operation 610, the plurality of discrete locations of the trajectory path model that will be used for sampling the radiotherapy radiation source are selected. The particular number of sampling locations may be varied. However, the number of sampling locations selected should provide sufficient data to ensure a reliability of the embodiments herein.

At operation 615, the physical components of the radiotherapy system are moved to a first one of the plurality of discrete locations. Such components typically include gantry 115 and imaging device 140, although other components may be included.

At 620, the 2D projection of fiducials 185 of phantom 180 irradiated by radiotherapy radiation source 150 on imaging device 140 is collected and stored. At 630, a determination is made whether a projection for all of the discrete sampling locations has been completed. If not, flow continues to operation 630 wherein the requisite physical components of the radiotherapy system are moved to the next 3D sampling location and a 2D projection is collected and stored as prescribed by operation 620.

In the instance the determination at 625 concludes all projections have been collected and stored, flow continues to operation 635 where corrections and/or filters may be applied to the 2D projections. The corrections are made to the "raw" 2D projections for compensation of detector characteristics, noise, up/down resampling, and/or other considerations.

At operation 640, the fiducials are detected in the collected and saved 2D projections and the fiducials in each 2D projection is related to the fiducials in 3D coordinate system associated with the phantom.

At 650, a determination is made whether there is sufficient projection information to proceed further with the process. Sufficient projection information may not have been obtained in the instance, for example, the cones of the radiotherapy radiation do not sufficiently pass through the phantom and irradiated the fiducials therein. In the event there is not sufficient projection information, then all of the projections with insufficient information may be rejected.

In the event there is sufficient projection information, the flow proceeds to 660 wherein a projection matrix is determined from the projection image corresponding to each discrete sampling location of the trajectory path model. The projection matrices determine the 2D coordinate of the projection in the projection of any 3D point in the coordinate system associated with the phantom generated by the radiotherapy source at that discrete location in the trajectory path model.

At operation 665, an actual, true, coordinate of the radiotherapy radiation source in the coordinate system associated with the phantom is determined at each sampling location, based on the projection matrix determined at operation 660. The actual true coordinate is thus a 3D representation of the location of the radiotherapy radiation source.

At operation 670, the trajectory path model of the radiotherapy radiation source is "fit" to the determined actual coordinate position of the radiotherapy radiation source at the plurality of discrete sampling locations included in process 400.

At operation 675, an output providing a presentation of some indicator of a variance between the trajectory path model of the radiotherapy radiation source and the determined actual coordinate position of the radiotherapy radiation source at the plurality of discrete sampling locations is provided.

The several embodiments described herein are solely for the purpose of illustration. Therefore, persons in the art will recognize from this description that other embodiments may be practiced with various modifications and alterations.

What is claimed is:

1. A method for determining a trajectory of a radiotherapy radiation source, the method comprising:
   obtaining a trajectory path model for a radiotherapy radiation source, the trajectory path model defined by at least one parameter;
   obtaining a plurality of discrete sample locations on the trajectory path model;
   providing a phantom having one or more fiducials at known reference positions in a coordinate system associated with the phantom;
   obtaining a projection image of the fiducials irradiated by the radiotherapy radiation source at each discrete location that samples the trajectory path model;
   determining, using a processor, a projection matrix from the projection image corresponding to each discrete location of the trajectory path model, the projection matrix determining the two dimensional coordinate of the projection in the projection image of a three dimensional point in the coordinate system associated with the phantom generated by the radiotherapy source at that discrete location in the trajectory path model;
   determining, using the processor, an actual coordinate of the radiotherapy radiation source in the coordinate system associated with the phantom at each of the discrete locations, based on the determined projection matrices;
   correlating the trajectory path model of the radiotherapy radiation source to the determined actual position of the radiotherapy radiation source at the plurality of discrete locations; and
   providing an output of at least one variance between the trajectory path model of the radiotherapy radiation source and the determined actual position of the radiotherapy radiation source at the plurality of discrete locations.

2. The method of claim 1, wherein the trajectory path model is one of a circular trajectory and a non-circular trajectory.

3. The method of claim 1, further comprising determining each of the plurality of discrete locations.

4. The method of claim 1, wherein the obtaining of a projection image of the fiducials irradiated by the radiotherapy radiation source at each discrete location comprises:
  moving the radiotherapy radiation source to each of the discrete locations;
  irradiating the phantom by the radiotherapy radiation source;
  detecting the projections of the fiducials irradiated by the radiotherapy radiation source at each of the discrete locations; and
  storing the detected projections of the fiducials at each of the discrete locations as a two-dimensional projection image.

5. The method of claim 4, further comprising relating the fiducials in each of the two-dimensional projection images in the coordinate system associated with the phantom to three-dimensional space in the coordinate system associated with the phantom.

6. The method of claim 1, wherein the correlating of the trajectory path model of the radiotherapy radiation source to the determined actual position of the radiotherapy radiation source at the plurality of discrete locations comprises fitting the trajectory path model to the determined actual position of the radiotherapy radiation source at the plurality of discrete locations.

7. The method of claim 6, wherein the fitting comprises using a least squares fitting procedure to fit the trajectory path model to the determined actual position of the radiotherapy radiation source at the plurality of discrete locations.

8. The method of claim 1, wherein the providing of an output comprises providing at least one of a numerical and a graphical presentation of a variance in trajectory and the at least one parameter of the trajectory path model for the determined actual position of the radiotherapy radiation source at the plurality of discrete locations.

9. The method of claim 1 further comprising an imaging calibration procedure.

10. A system comprising:
  a first radiation-based imaging system to emit radiation; and
  a processing device to:
    obtain a trajectory path model for a radiotherapy radiation source, the trajectory path model defined by at least one parameter;
    obtain a plurality of discrete sample locations on the trajectory path model;
    provide a phantom having one or more fiducials at known reference positions in a coordinate system associated with the phantom;
    obtain a projection image of the fiducials irradiated by the radiotherapy radiation source at each discrete location that samples the trajectory path model;
    determine a projection matrix from the projection image corresponding to each discrete location of the trajectory path model, the projection matrix determining the two dimensional coordinate of the projection in the projection image of a three dimensional point in the coordinate system associated with the phantom generated by the radiotherapy source at that discrete location in the trajectory path model;
    determine an actual coordinate of the radiotherapy radiation source in the coordinate system associated with the phantom at each of the discrete locations, based on the determined projection matrices;
    correlate the trajectory path model of the radiotherapy radiation source to the determined actual position of the radiotherapy radiation source at the plurality of discrete locations; and
    provide an output of at least one variance between the trajectory path model of the radiotherapy radiation source and the determined actual position of the radiotherapy radiation source at the plurality of discrete locations.

11. The system of claim 10, wherein the trajectory path model is one of a circular trajectory and a non-circular trajectory.

12. The system of claim 10, wherein the processor further determines each of the plurality of discrete locations.

13. The system of claim 10, wherein the obtaining of a projection image of the fiducials irradiated by the radiotherapy radiation source at each discrete location comprises:
  moving the radiotherapy radiation source to each of the discrete locations;
  irradiating the phantom by the radiotherapy radiation source;
  detecting the projections of the fiducials irradiated by the radiotherapy radiation source at each of the discrete locations; and
  storing the detected projections of the fiducials at each of the discrete locations as a two-dimensional projection image.

14. The system of claim 13, wherein the processor further relates the fiducials in each of the two-dimensional projection images in the coordinate system associated with the phantom to three-dimensional space in the coordinate system associated with the phantom.

15. The system of claim 10, wherein the correlating of the trajectory path model of the radiotherapy radiation source to the determined actual position of the radiotherapy radiation source at the plurality of discrete locations comprises fitting the trajectory path model to the determined actual position of the radiotherapy radiation source at the plurality of discrete locations.

16. The system of claim 15, wherein the fitting comprises using a least squares fitting procedure to fit the trajectory path model to the determined actual position of the radiotherapy radiation source at the plurality of discrete locations.

17. The system of claim 10, wherein the providing of an output comprises providing at least one of a numerical and a graphical presentation of a variance in trajectory and the at least one parameter of the trajectory path model for the determined actual position of the radiotherapy radiation source at the plurality of discrete locations.

* * * * *